(12) United States Patent
Tjassens et al.

(10) Patent No.: US 9,669,187 B2
(45) Date of Patent: Jun. 6, 2017

(54) MALE URINARY CATHETER PACKAGE

(71) Applicant: Curan Medical B.V., Doetinchem (NL)

(72) Inventors: Nathalie Tjassens, Doetinchem (NL); David van Groningen, Doetinchem (NL); Ad van Velthoven, Beusichem (NL)

(73) Assignee: CURAN MEDICAL B.V., Doetinchem (NL)

( * ) Notice: Subject to any disclaimer, the term of this patent is extended or adjusted under 35 U.S.C. 154(b) by 388 days.

(21) Appl. No.: 14/329,015

(22) Filed: Jul. 11, 2014

(65) Prior Publication Data
US 2015/0018803 A1   Jan. 15, 2015

(30) Foreign Application Priority Data

Jul. 12, 2013   (EP) .................................... 13176283

(51) Int. Cl.
*A61M 25/00* (2006.01)
*A61M 25/01* (2006.01)

(52) U.S. Cl.
CPC ....... *A61M 25/002* (2013.01); *A61M 25/0111* (2013.01); *A61M 2025/0062* (2013.01);
(Continued)

(58) Field of Classification Search
CPC ............ A61M 25/002; A61M 25/0111; A61M 2025/0062; A61M 2207/00; A61M 2210/1096; A61M 2210/167; A61M 2025/0175; A61B 42/40; A61B 50/30; A61B 2050/3006; A61B 2050/3013; A61B 2050/3014; B65D 1/0292; B65D 11/18; B65D 1/44; B65D 21/086; B65D 47/061;
(Continued)

(56) References Cited

U.S. PATENT DOCUMENTS

| 5,217,114 A * | 6/1993 | Gadberry | ............ A61M 25/002 206/364 |
| 6,578,709 B1 | 6/2003 | Kavanagh et al. | |

(Continued)

FOREIGN PATENT DOCUMENTS

| DK | EP 1023882 A1 * | 8/2000 | ............... A61F 5/44 |
| EP | 2106821 | 10/2009 | |

(Continued)

OTHER PUBLICATIONS

Machine translation of JP 2011139882 A, Google Translate Tue Jan. 31, 2017.*
Search Report from European Application No. 13176283.3.

*Primary Examiner* — Adam Marcetich
(74) *Attorney, Agent, or Firm* — Volpe and Koenig, P.C.

(57) ABSTRACT

Package (10) for holding an intermittent, male urinary catheter (1). The package (10) has a vessel (5) which is tubular in shape allowing the urinary catheter (1) to be movably arranged in an inner volume of the vessel (5). An enveloping housing of the package entirely encloses the urinary catheter (1) when packaged. The enveloping housing has three tubular parts (2, 3, 6) of which a first and second straight part (2, 3) are of a hard plastic material, and a third part (6) is of a flexible material. The first straight (2) part is closed off at a bottom end thereof and the second straight part (3) is closeable by the cap (4) and comprises the vessel (5).

14 Claims, 3 Drawing Sheets

(52) U.S. Cl.
CPC . *A61M 2025/0175* (2013.01); *A61M 2207/00* (2013.01); *A61M 2210/1096* (2013.01); *A61M 2210/167* (2013.01)

(58) Field of Classification Search
CPC  F16L 11/15; F16L 11/11; F16L 11/111; F16L 51/02; F16L 51/025; F16L 51/03
See application file for complete search history.

(56) References Cited

U.S. PATENT DOCUMENTS

| | | | | |
|---|---|---|---|---|
| 2001/0001443 | A1* | 5/2001 | Kayerod | A61L 29/085 206/364 |
| 2005/0178684 | A1* | 8/2005 | Kesler | A61M 25/002 206/364 |
| 2006/0025753 | A1* | 2/2006 | Kubalak | A61M 25/0017 604/544 |
| 2006/0163097 | A1* | 7/2006 | Murray | A61M 25/0009 206/364 |
| 2008/0119803 | A1* | 5/2008 | Lund | A61F 5/4404 604/327 |
| 2009/0008279 | A1* | 1/2009 | Tanghoej | A61M 25/002 206/364 |
| 2009/0299334 | A1 | 12/2009 | Nishtala et al. | |
| 2011/0290756 | A1* | 12/2011 | Horstman | B65D 39/08 215/329 |
| 2012/0110951 | A1* | 5/2012 | van Groningen | A61M 25/0111 53/425 |
| 2013/0138088 | A1* | 5/2013 | Nielsen | A61L 29/14 604/544 |
| 2013/0161227 | A1* | 6/2013 | Gustavsson | A61M 25/002 206/571 |
| 2013/0186778 | A1* | 7/2013 | Terry | A61M 25/002 206/210 |
| 2015/0250544 | A1* | 9/2015 | Costargent | A61M 25/0111 248/49 |

FOREIGN PATENT DOCUMENTS

| | | | | |
|---|---|---|---|---|
| JP | 2011139882 | | 7/2011 | |
| SE | EP 2106821 | A1 * | 10/2009 | A61M 25/0017 |
| WO | WO 9204932 | A1 * | 4/1992 | A61M 25/0111 |
| WO | 2012060699 | | 5/2012 | |

* cited by examiner

MALE URINARY CATHETER PACKAGE

CROSS REFERENCE TO RELATED APPLICATION

This application claims the benefit of European application number 13176283.3 filed Jul. 12, 2013, which is incorporated by reference as if fully set forth.

FIELD OF INVENTION

The present invention relates to a male urinary catheter package, more particularly to a compact male device for intermittent self catheterization. In a further aspect, the present invention relates to a method of assembling the male urinary catheter package.

BACKGROUND

International application WO 2012/060699 A1 of the same applicant as the present invention discloses a package for a female urinary catheter. The package comprises a container enclosing a female urinary catheter in its entirety.

European patent application EP 1 023 882 A1 discloses a urinary catheter assembly, wherein the assembly comprises a flexible tubular catheter package provided with elongation means at parts of the catheter package. More particular, the elongation means comprise click-clack or soft corrugations in the same material of the flexible tubular catheter package itself.

A similar arrangement is disclosed in European patent application EP 2 106 821 A1, wherein a tubular member is used for storing a catheter before use and for elongating the catheter during actual use. The single material tubular member is provided with one or more regions with a plurality of pleats, allowing curvature of the tubular member (with the catheter inside) in a packaged state.

SUMMARY

Catheterization is a procedure to empty a bladder by inserting a urinary catheter to collect urine. For clean intermittent self catheterization (CISC) the urinary catheter does not remain inside the bladder indefinitely but only for a time necessary to empty the bladder after which it is removed. CISC is a procedure that is used for avoiding problems that may occur due to various conditions, disturbances and/or injuries of the nervous system, such as non-neurogenic bladder dysfunction or intravesical obstruction with incomplete bladder evacuation. CISC can be implemented as a one-time treatment, a repeated treatment over a short period of time, or a lifelong treatment. Intermittent catheterization is often preferred to indwelling catheterization, because they can result in a better quality of life for the patient or subject and has less complications, such as various urinary tract infections and/or urethral strictures.

The present invention seeks to provide a male urinary catheter package that allows for a compact, discrete and sterile storage of a urinary catheter, in particular a male intermittent urinary catheter. The present invention further seeks to provide a male urinary catheter package that allows for easy, comfortable, and risk free insertion and withdrawal of the urinary catheter.

According to a first aspect of the present invention, a male (intermittent) unitary catheter package according to the preamble defined above is provided, wherein the package comprises a vessel positioned in an inner volume of the package, the vessel being tubular in shape with a first and second opening allowing the (intermittent) urinary catheter to be movably arranged in an inner volume of the vessel; an enveloping housing entirely enclosing the (intermittent) urinary catheter when packaged, the enveloping housing comprising at least three tubular parts for accommodating the (intermittent) urinary catheter, wherein a first and second straight part of the at least three tubular parts are of a hard plastic material, and a third part is of a flexible material; an inner lumen of the third part interconnecting inner lumens of the first and second straight part; a cap for providing access to an inner volume of the package, and the first straight part being closed off at a bottom end thereof and the second straight part being closeable by the cap and comprising the vessel.

The male (intermittent) urinary catheter package of the present invention provides a professional looking, rugged and hygienic device for intermittent self catheterization, wherein the catheter package offers a small form factor due to the fact that the package is foldable by means of the flexible third part. The integrated vessel provides a lubrication agent or activating fluid, so that users have a complete intermittent self catheterization solution as no separate pouch or container for lubricant or activator is needed. Further, the cap allows sterilization gas from outside the catheter package to pass into the inner volume of the package, so that sterility of the urinary catheter is guaranteed as the enveloping housing completely and hermetically encloses the urinary catheter in the sterilized inner volume.

In an embodiment, the third part may comprise a pleated or corrugated wall, so that flexibility may be further increased in addition to the flexibility of the material of the third part in itself. The pleated or corrugated wall also provides a convenient way for keeping the catheter package folded, although a holding element may be used for keeping the catheter package folded.

For an appealing visual appearance, in an embodiment the length of the first straight part is substantially equal to the length of the second straight part in combination with the cap fitted thereon. In this embodiment, folding the catheter package reduces the length of an unfolded catheter package to about a half, allowing relatively long male urinary catheters to be stored compactly.

In advantageous embodiments, the vessel may comprise a lubricant for the urinary catheter, and has a distal end with an aperture having a diameter substantially similar to an outer diameter of the urinary catheter, and a proximal end with an aperture having a diameter larger than the outer diameter of the catheter tube. This embodiment prevents leakage of lubricant or activating fluids out of the vessel into other parts of the inner volume of the package, but it also ensures an even spreading of said lubricant or activating fluid when the urinary catheter is taken out from the package. Note that the catheter package of the present invention is also suitable for hydrophilic catheters, thus wherein the urinary catheter comprises a hydrophilic coating and the vessel comprises an activating fluid (e.g. water) and a seal element at the proximal end.

In an embodiment, the package further comprises an insertion device surrounding the urinary catheter. Typically, the insertion device may be slidably disposed around the catheter, and may be substantial flexible and squeezable, such as a rubber-like slidable tube disposed around the catheter. The insertion device allows a patient or user to touch and clamp the catheter tube between two or more fingers without actually touching the catheter surface and thus maintaining sterility.

In a further aspect, the present invention seeks to provide a method for assembling a package for a urinary catheter, the method comprising providing an enveloping housing entirely enclosing the urinary catheter by attaching at least three tubular parts to each other, wherein a first and second straight part of the at least three tubular parts are of a rigid material, and a third part is of a flexible material, the first straight part being closed off at a bottom end thereof, and by attaching the third part to the first straight part and the second straight part; inserting a vessel for holding a preparation substance for the urinary catheter into a lumen of the second straight part; closing off an inner volume of the package by attaching a cap to the second straight part.

In an embodiment, before closing off the inner volume by attaching the cap, the method further comprises sterilizing an inner volume of the package using a sterilizing agent, such as Ethylene Oxide, inserting the urinary catheter into the inner lumen, and filling the vessel with a substance, such as a lubricating gel or activating fluid, after inserting the urinary catheter in the package.

The method provides a rugged, foldable package holding a fully sterilized urinary catheter which is lubricated, or activated in hydrophilic sense, when taken out of the package.

BRIEF DESCRIPTION OF THE DRAWINGS

The present invention will be discussed in more detail hereinafter by way of a number of exemplary embodiments with reference to the attached drawings, in which.

DETAILED DESCRIPTION

Figure 1:
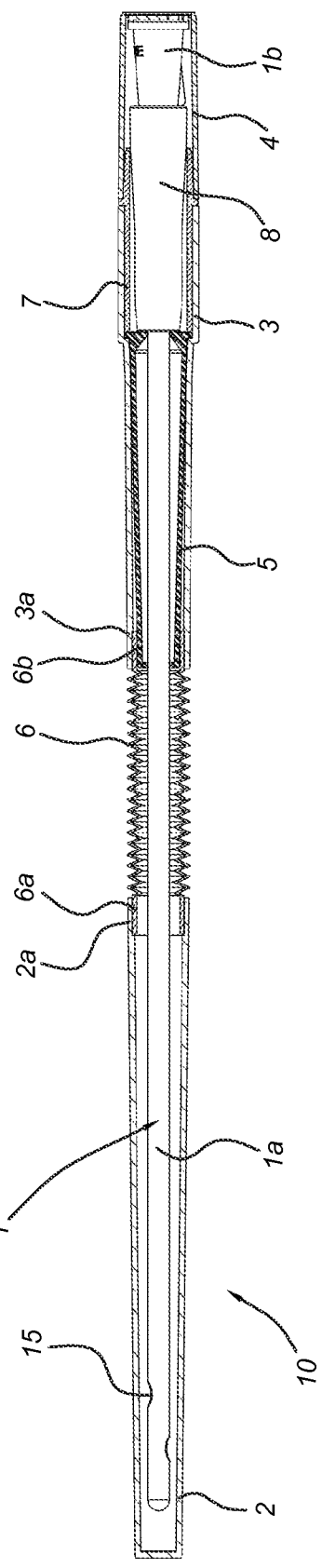
FIG. 1 shows a cross sectional view of an embodiment of a male urinary catheter package according to the present invention.

FIG. 1 shows a cross sectional view of an embodiment of a male (intermittent) urinary catheter package 10 according to the present invention. In the embodiment shown, a urinary catheter 1 is stored within the package 10, wherein the urinary catheter 1 comprises a catheter tube 1a having apertures 15 and a drainage funnel 1b through which bladder content is evacuated during a catheterization procedure, especially suited for intermittent self-catheterization.

The depicted package 10 comprises an enveloping housing entirely enclosing the (intermittent) urinary catheter 1 when packaged. The enveloping housing comprises at least three tubular parts 2, 3, 6 for accommodating the urinary catheter 1, wherein a first straight part 2 and a second straight part 3 of the at least three tubular parts 2, 3, 6 are of an inflexible material, such as hard plastic, and a third part 6 of the at least three tubular parts 2, 3, 6 is of a flexible (bendable, foldable) material.

The first and second straight part 2, 3 are substantially inflexible tubular components that cannot be folded by hand. More precisely, the first and second straight part 2, 3 are for all intents and purposes stiff, rigid, hard or rigid tubular components if one were to try to fold or bend said first and said second straight part 2, 3 by hand. In typical embodiments, the first and second straight part 2, 3 are made of a hard or rigid plastic material, such as a Methacrylate/Butadiene/Styrene Polymer, or MBS for short.

In the embodiment shown, the third part 6 comprises a pleated or corrugated wall, wherein the pleated or corrugated wall may provide further flexibility. In an embodiment, the third part 6 is made of a polypropylene (PP) or polyethylene (PE) material. In a further embodiment, the third part 6 is made of a translucent material, such as a translucent blue colour material for providing a pleasing visual appearance, and allowing easy inspection of the contents of the package 10. The third part 6 is e.g. manufactured through an extrusion process.

The at least three tubular part 2, 3, 6 are connected such that an inner lumen of the third part 6 interconnects inner lumens of the first and second straight part 2, 3, wherein the first straight 2 part is closed off at a bottom end thereof. The at least three tubular part 2, 3, 6 provide an elongated cavity within the at least three tubular parts 2,3,6 for accommodating the (intermittent) urinary catheter 1.

The enveloping housing further comprises a cap 4 for allowing or restricting access to an inner volume of the package 10. Here, the inner volume of the package 10 shall be construed as being a volume comprised by the at least three tubular parts 2, 3, 6 and cap 4 when assembled together. The cap 4 is removeably attached to the second straight part 3 and closes off the inner volume of the package 10.

According to the present invention, the package 10 further comprises a tubular vessel 5 disposed in the inner volume of the package 10, or more specifically, the vessel 5 is disposed within the enveloping housing. In advantageous embodiments, the second straight part 3 comprises the vessel 5, wherein the vessel 5 is disposed in the third straight part 3. The vessel 5 is tubular in shape and comprises a first and second opening allowing the urinary catheter 1 to be movably arranged in an inner volume (lumen) of the vessel 5. In typical embodiments, the vessel 5 may comprise a lubricant, gel, water or another activator for facilitating comfortable and risk free insertion and withdrawal of the urinary catheter 1 through the urinary tract. Note that the first and second opening of the vessel 5 provide sufficient clearances around the urinary catheter 1 when packaged, so that the first and second opening allow for a movable arrangement of the urinary catheter 1 within the vessel 5.

Figure 6:
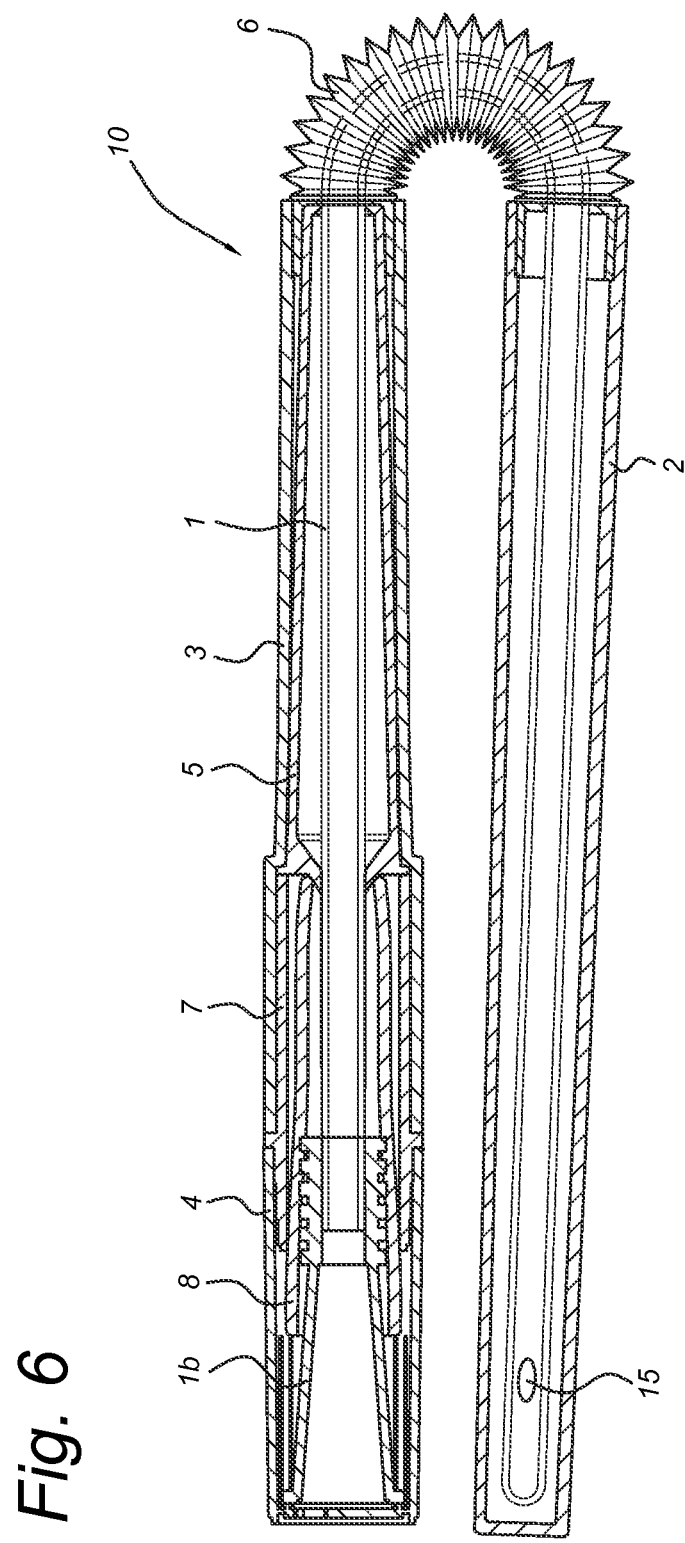
FIG. 6 shows a cross sectional view of an embodiment of a folded male urinary catheter package according to the present invention.

In actual use, a patient or subject is able to fold the package 10 from a substantially straight configuration as depicted in FIG. 1 to a U-shaped configuration as shown in FIG. 6, wherein the first and second straight part 2, 3 are arranged in a parallel fashion. Because male urinary catheters are generally longer than e.g. female urinary catheters, the foldable package 10 of the present invention provides a convenient way for compactly packaging a long urinary catheter. For example, the first straight part 2 may be held in one hand whereas the second straight part 3 with cap 4 may be held in another hand. Since the first and second straight part 2, 3 are rigid, the flexible third part 6 makes it possible to fold the package 10 into a U-shape as depicted in FIG. 6.

The package 10 may further comprise a holding element for keeping the package 10 in a folded state. The holding element may comprise one of: a tape, an (elastic) band, a string, a hook-and-loop fastener (e.g. Velcro), a releasable glue connection, a snap-fit element, and the like.

Further, in the embodiment shown in FIG. 1, the third part 6 and first straight part 2, and third part 6 and second straight part 3 are connected at their respective circumferential ends 2a, 6a, 3a, 6b, wherein the connection at the circumferential ends 2a, 6a, 3a, 6b may be a glued connections, a chemical connection, a welded connection, a press-fit connection, a threaded connection, a bayonet connection and the like.

To provide a compact package 10, in an advantageous embodiment the length of the first straight part 2 is substantially equal to the length of the second straight part 3 in combination with the cap 4 fitted thereon. This embodiment allows for a folded size/length of the package 10 of about half the length of the urinary catheter 1.

The package 10 of the present invention further comprises a connector 7 having a generally tubular shape, with a first end for holding the vessel 5 in place in the second straight part 3, and a second end for receiving the cap 4, wherein the connector 7 and second straight part 3 are in a clamping relationship. For example, the connector 7 and the straight part 3 may be connected using a press-fit connection that provides a sufficiently large clamping force for securing the vessel 5 within the second straight part 3.

In view of the invention, self catheterization should be risk free with regard to various types of viral, bacterial and/or fungal infections while using the urinary catheter 1. In order to maintain maximum sterility of the urinary catheter 1, the patient or user should not touch the urinary catheter 1, in particular the catheter tube 1a, prior to or during insertion of said catheter into the urinary tract. To that end, the package 10 further comprises an insertion device 8 surrounding the urinary catheter 1. For example, the package 10 may comprise an insertion device 8 moveably arranged around the urinary catheter 1. In typical embodiments, the package 10 comprises an insertion device 8 slidably arranged around the urinary catheters 10, wherein the insertion device 8 may be a flexible tubular component which is squeezable by e.g. two or more fingers. In an embodiment, the insertion device 8 may be mode of a rubber-like material.

The insertion device 8 is particularly advantageous as it avoids contact by hand or fingers with the outer surface of the urinary catheter 1 during insertion or withdrawal of said catheter. For example, the user may clamp the insertion device 8 around the catheter tube 1a between two or more fingers for moving the urinary catheter 1 into or out of the urinary tract.

Figure 2:
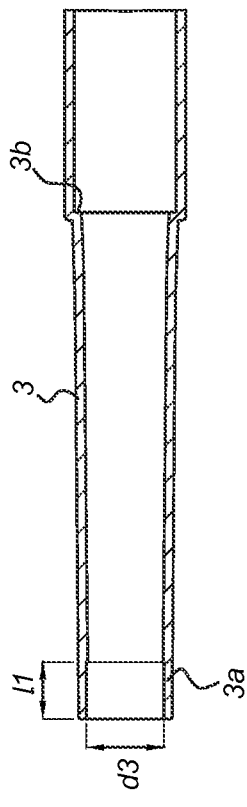
FIG. 2 shows a cross sectional view of an embodiment of a second straight part according to the present invention.

FIG. 2 shows a cross sectional view of an embodiment of a second straight part 3 according to the present invention. In the embodiment shown, the second straight part 3 comprises a circumferential end 3a having an inner diameter d3 of length 11 matching the circumferential end 6b of the third part 6 as shown in FIG. 1. The second straight part 3 further comprises a fixation end 3b through which he vessel 5 is received and secured by the connector 7.

In an embodiment, the second straight part 3 comprises an insertion device area or inner volume for accommodating at least a part of the insertion device 8. In a further embodiment, the second straight part 3 comprises a vessel area or inner volume for accommodating the vessel 5, wherein the vessel area or inner volume of the second straight part 3 is positioned between the circumferential end 3a and the fixation end 3b of said second straight part. The vessel area of the second straight part 3 is configured as wide as possible for ensuring that the vessel 5 can be as large as possible. The fixation end 3b is adapted to keep the vessel 5 in place, wherein the vessel 5 is further immobilized and fixedly arranged by the connector 7 as depicted in FIG. 1. The insertion device area of the second straight part 3 is configured to be as small as possible but large enough for accommodating at least a part of the connector 7 and insertion device 8.

In an embodiment, the second straight part 3 is made of a hard plastic material, such as MBS. In a further embodiment, the second straight part 3 may be made of a translucent material, such as a translucent blue material for providing a clean, hygienic and professional look to a patient or user. In most embodiments, the second straight part 3 is conveniently manufactured through an injection moulding process.

Figure 3:
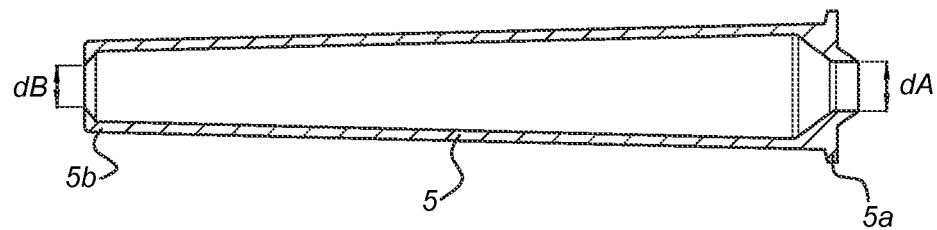
FIG. 3 shows a cross sectional view of an embodiment of a vessel according to the present invention.

FIG. 3 shows a cross sectional view of an embodiment of a vessel 5 according to the present invention. In the embodiment shown, the vessel 5 may compromise a lubricant and/or activator substance for the urinary catheter 1. Further, the vessel 5 may also comprise a distal end 5b with an aperture having a diameter dB substantially similar to an outer diameter of the urinary catheter 1, and a proximal end 5a with an aperture having a diameter dA larger than the outer diameter of the catheter tube 1a.

The aperture of the distal end 5b provides a snug and relatively tight fit around the catheter tube 1a, preventing leakage when the vessel 5 is being filled with a lubricant and/or an activator substance during the packaging process of the package 10, and during storage of the package 10 with catheter 1. On the other hand, the aperture of the proximal end 5a provides a relatively loose fit around the catheter tube 1a for ensuring an even spreading of the lubricant and/or activator substance when the catheter tube 1a is removed from the package 10.

To further explain this last point, as shown in FIG. 3, the vessel 5 may comprise a tapered geometry along a longitudinal direction, wherein an inner diameter of the vessel 5 at the distal end 5b is smaller than an inner diameter of the vessel 5 at the proximal end 5a. Such a tapered geometry has the surprising effect that a lubricant and/or activating fluid within the vessel 5 tends to accumulate near the aperture of the proximal end 5a when the catheter tube 1a is pulled from the package 10. Furthermore, since the aperture at the proximal end 5a has a diameter dA larger than the outer diameter of the catheter tube 1a, an even spreading of the lubricant and/or activator substance on the catheter tube 1a is guaranteed when the urinary catheter 1 is pulled from the package 10.

The proximal end 5a of the vessel 5 is provided with an abutment flange 5a configured for abutting the fixation end 3b of the second straight part 3 as well as the connector 7, thereby firmly immobilizing the vessel 5 within the second straight part 3.

In a further embodiment the urinary catheter 1 comprises a hydrophilic coating, and the vessel 5 comprises an activating fluid (e.g. water); the vessel 5 further comprising a seal element at the proximal end 5a and/or distal end, ensuring no leakage of activating fluid once the package 10 is completed with the catheter 1. The package 10 of the present invention is not limited to non-hydrophilic catheters 1 requiring a lubricant, but it is also suitable for hydrophilic catheters 1 requiring an activating substance or fluid. In an embodiment, the vessel 5 is made of silicone and manufactured through an injection moulding process.

Figure 4:
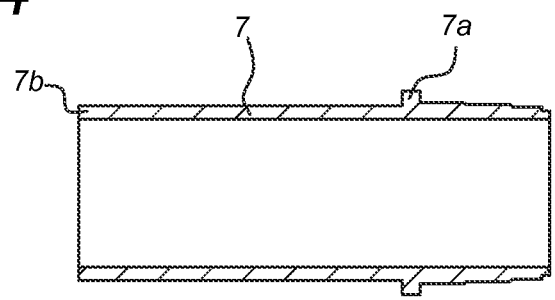
FIG. 4 shows a cross sectional view of an embodiment of a connector according to the present invention.

FIG. 4 shows a cross sectional view of an embodiment of a connector 7 according to the present invention. In the embodiment shown, the connector 7 is tubular in shape and may comprise a fixation end 7b for immobilizing the vessel 5 within the second straight part 3. As mentioned earlier, the connector 7 and second straight part 3 are advantageously connected by means of a clamped or press-fit arrangement thereof, wherein at least a part the connector 7 is tightly and fixedly fitted within the second straight part 3.

In an embodiment, the connector 7 may further comprise an abutment ridge 7a which abuts the second straight part 3 as well as the cap 4 when the cap 4 is fitted over the connector 7. In a further embodiment the connector 7 may comprise a tapered end, such as a stepped tapered end. The cap 4 and tapered end of the connecter 7 allow for a clamped arrangement thereof. As a result, when sliding the cap 4 over the connector 7 for closing off the inner volume of the package 10, a clamping force increases when the cap 4 is moved further over the tapered end toward the abutment ridge 7a. In an embodiment, the connector 7 is made of Thermoplastic Polyurethane (TPU) in a translucent colour, such as a visually appealing translucent blue colour. The connector 7 is e.g. manufactured through an injection moulding process.

Figure 5:
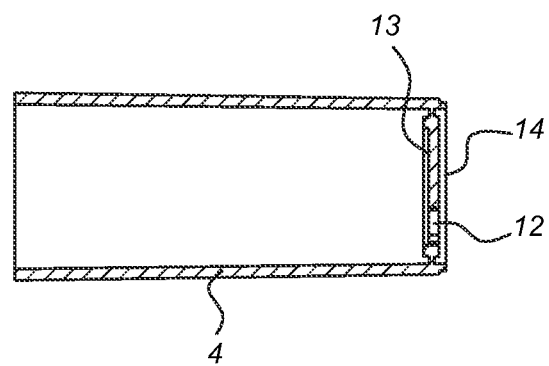
FIG. 5 shows a cross sectional view of an embodiment of a cap according to the present invention.

FIG. 5 shows a cross sectional view of an embodiment of a cap 4 according to the present invention. In this embodiment, the cap 4 is tubular in shape and comprises an open end (left) and a closed end(right). In an advantageous embodiment the cap 4 comprises a plurality of apertures 12 for sterilization and disinfection of the entire inner volume of the package 10 after assembly thereof, wherein an Ethylene Oxide (EtO) sterilization process is particularly suitable for the package 10.

The cap 4 may also comprise a permeable membrane 13 covering the plurality of apertures 12, wherein the permeable membrane allows sterilization gases from outside the package 10 to pass through into the inner volume of the package 10 while maintaining sterility once the sterilization process is completed. After sterilization, the package 10 can be completely sealed using a sealing member 14 at the outside surface of the cap 4.

In an embodiment, the cap 4 is made of a resin, such as a BASF-K Resin, which is a transparent material with a shiny surface and provides a hygienic and clean look. The cap 4 is typically injection moulded. In a further embodiment, an inner diameter near the open end of the cap 4 is slightly smaller than a largest outer diameter of the tapered end of the connector 7 adjoining the abutment ridge 7a. As a result, the cap 4 tightly fits over the connector 7 but can be easily removed by hand.

In a further aspect, the present invention relates to a method of assembling a package 10 for a urinary catheter 1. The method comprises providing an enveloping housing entirely enclosing the urinary catheter 1 by attaching at least three tubular parts 2,3,6 to each other, wherein a first and second straight part 2, 3 of the at least three tubular parts 2, 3, 6 are of a rigid material, and a third part 6 is of a flexible material, the first straight 2 part being closed off at a bottom end thereof, and by attaching the third part 6 to the first straight part 2 and the second straight part 3; inserting a vessel 5 for holding a preparation substance for the urinary catheter (1) into a lumen of the second straight part (3); closing off an inner volume of the package by attaching a cap (4) to the second straight part (3).

The above method for assembling a male unitary catheter package 10 allows for a straightforward assembly process that can be readily mechanized. In essence the at least three tubular parts 2,3,6 are assembled first, then the vessel 5 is inserted into the second straight part 3, e.g. inserted into an inner cavity of said part 3. Finally the cap 4 is provided and attached to the second straight part 3, wherein the cap 4 is slid over the second straight part 3 and kept in place by a clamped or press-fit arrangement thereof. The resulting package 10 completely encloses the inner volume of said package 10.

In an embodiment, before closing off the inner volume by attaching the cap 4, the method further comprises sterilizing the inner volume of the package 10 using a sterilizing agent, such as Ethylene Oxide; inserting the urinary catheter 1 (already sterilized, possibly in combination with the optional insertion device 8) into the inner lumen, and filling the vessel 5 with a substance after inserting the urinary catheter 1 in the package 10. The vessel 5 is typically filled with a lubricating gel, an activating fluid such as water, or another suitable medium.

This method step is particularly advantageous for the embodiment of a vessel 5 shown in FIG. 3. Since the inner diameter dB of the vessel 5 has a tight and snug fit with an outer diameter of the catheter tube 1a, filling the vessel 5 with a lubrication agent or activating fluid avoids leakage into the inner volume of the package 10, in particular the first straight part 2 and third part 6.

After this method step, the vessel 5 is largely disposed within the second straight part 3 and may be affixed thereto using a connecter 7 as embodied in FIG. 4. In an embodiment, inserting the vessel 5 comprises fixing the vessel 5 inside the second straight part 3 using a connector 7, the connector 7 having a generally tubular shape, with a first end for holding the vessel 5 in place in the second straight part 3 and a second end forming a receiving end for the cap 4, wherein the connector 7 and second straight part 3 are in a clamping relationship.

The present invention embodiments have been described above with reference to a number of exemplary embodiments as shown in the drawings. Modifications and alternative implementations of some parts or elements are possible, and are included in the scope of protection as defined in the appended claims.

What is claimed is:

1. A package for holding a urinary catheter, the package comprising:
  A separate vessel positioned in an inner volume of the package, the vessel being tubular in shape with a first and second opening allowing the urinary catheter to be movably arranged in an inner volume of the vessel;
  an enveloping housing entirely enclosing the urinary catheter when packaged, the enveloping housing comprising:
    at least three separate tubular parts for accommodating the urinary catheter, wherein a first and second straight part of the at least three tubular parts are made of a hard plastic material, and a third part is made of a flexible material;
    an inner lumen of the third part interconnecting inner lumens of the first and second straight part;
    a cap for providing access to an inner volume of the package, and
    the first straight part being closed off at a bottom end thereof and the second straight part being closeable by the cap and comprising the vessel.

2. The package of claim 1, wherein the third part is made of a polypropylene or polyethylene material and comprises a pleated or corrugated wall.

3. The package of claim 1, wherein the third part and first straight part, and third part and second straight part are connected at their respective circumferential ends.

4. The package of claim 1, wherein the length of the first straight part is substantially equal to the length of the second straight part in combination with the cap fitted on the second straight part.

5. The package of claim 1, the package further comprising a connector having a generally tubular shape, with a first end for holding the vessel in place in the second straight part, and a second end for receiving the cap, wherein the connector and second straight part are in a clamping relationship.

6. The package of claim 1, wherein the vessel comprises a lubricant for the urinary catheter, has a distal end with an aperture having a diameter dB substantially similar to an outer diameter of the urinary catheter, and a proximal end with an aperture having a diameter dA larger than the outer diameter of the catheter tube.

7. The package of claim 1, wherein the urinary catheter comprises a hydrophilic coating, and wherein the vessel comprises activating fluid; the vessel further comprising a seal element at the proximal end.

8. The package of claim 1, wherein the package further comprises an insertion device surrounding the urinary catheter.

9. The package of claim 1, wherein the cap comprises a plurality of apertures.

10. The package of claim 1, wherein the package further comprises a holding element for keeping the package in a folded state.

11. The package of claim 10, wherein the holding element comprises one of: a tape, a band, a string, a hook-and-loop fastener, a releasable glue connection, a snap-fit element.

12. A method for assembling a package for a urinary catheter, the method comprising:
    providing an enveloping housing entirely enclosing the urinary catheter by attaching at least three separate tubular parts to each other, wherein a first and second straight part of the at least three tubular parts are made of a rigid material, and a third part is made of a flexible material, the first straight part being closed off at a bottom end thereof, and by attaching the third part to the first straight part and the second straight part;
    inserting a separate vessel for holding a preparation substance for the urinary catheter into a lumen of the second straight part;
    closing off an inner volume of the package by attaching a cap to the second straight part.

13. The method of claim 12, further comprising, before closing off the inner volume by attaching the cap, sterilizing an inner volume of the package using a sterilizing agent; inserting the urinary catheter into the inner lumen, and filling the vessel with a substance after inserting the urinary catheter in the package.

14. The method of claim 12, wherein inserting the vessel comprises fixing the vessel inside the second straight part using a connector, the connector having a generally tubular shape, with a first end for holding the vessel in place in the second straight part and a second end forming a receiving end for the cap, wherein the connector and second straight part are in a clamping relationship.

* * * * *